(12) United States Patent
Sasaki et al.

(10) Patent No.: US 6,893,649 B2
(45) Date of Patent: May 17, 2005

(54) SOLID POWDER COSMETICS

(75) Inventors: Yuki Sasaki, Minamiashigara (JP); Yasuo Matsumura, Minamiashigara (JP)

(73) Assignee: Fuji Xerox Co., Ltd., Tokyo (JP)

(*) Notice: Subject to any disclaimer, the term of this patent is extended or adjusted under 35 U.S.C. 154(b) by 0 days.

(21) Appl. No.: 10/237,091

(22) Filed: Sep. 9, 2002

(65) Prior Publication Data

US 2003/0175227 A1 Sep. 18, 2003

(30) Foreign Application Priority Data

Mar. 14, 2002 (JP) ........................ 2002-070880

(51) Int. Cl.⁷ .................. A61K 7/00; A61K 7/035; A61K 7/021
(52) U.S. Cl. ................... 424/401; 424/69; 424/63
(58) Field of Search ..................... 424/401, 63, 69

(56) References Cited

U.S. PATENT DOCUMENTS

| | | | | |
|---|---|---|---|---|
| 5,496,543 A | * | 3/1996 | Lagrange et al. | 424/70.7 |
| 5,612,021 A | * | 3/1997 | Mellul | 424/61 |
| 5,681,877 A | * | 10/1997 | Hosotte-Filbert et al. | 524/32 |
| 6,207,174 B1 | * | 3/2001 | Hineno et al. | 424/401 |

FOREIGN PATENT DOCUMENTS

| | | |
|---|---|---|
| JP | A 5-310530 | 11/1993 |
| JP | A 8-165221 | 6/1996 |
| JP | A 8-277208 | 10/1996 |
| JP | A 10-338616 | 12/1998 |
| JP | A 11-209243 | 8/1999 |
| JP | A 11-228336 | 8/1999 |
| JP | A 2000-119134 | 4/2000 |
| JP | A 2001-151639 | 6/2001 |

* cited by examiner

*Primary Examiner*—James Spear
*Assistant Examiner*—Retford Berko
(74) *Attorney, Agent, or Firm*—Oliff & Berridge, PLC

(57) ABSTRACT

A solid powder cosmetic is provided which is superior in availability and formability. The solid powder cosmetic comprises 10 to 80 wt % of extender, 0.1 to 40 wt % of color pigment, and 0.5 to 80 wt % of spherical resin particles characterized by an average volume particle size of 2.0 to 20.0 μm, a glass-transition temperature of 10 to 100° C. and a number average molecular weight of 5000 to 20000. Further, the solid powder cosmetic has an average volume particle size distribution GSDv of the spherical resin particles being 1.3 or less, and a shape factor SF1 of the spherical resin particles being 100 to 140.

16 Claims, No Drawings

SOLID POWDER COSMETICS

BACKGROUND OF THE INVENTION

1. Field of the Invention

The present invention relates to solid powder cosmetics including make-up cosmetics such as foundations, face powders, eyebrows, eyeshadows, eyeliners, blushes, and powders, and powder washes and facial washes, and to a cosmetic which has a spherical, smooth surface, and which accomplishes smooth and uniform spread and a dry feel by blending resin particles having a uniform particle size.

2. Description of the Related Art

Conventionally, solid powder cosmetics have been widely used as cosmetics for correcting facial marks such as pimples, wrinkles, or pores and for adding shadow to lines on a face. However, if a large amount of a cosmetic is applied in order to enhance an effect such as coloring or covering, the applied layer becomes thick, increasing the likelihood that the makeup will create an unnatural impression and cause irregularity in color. These are significantly evident when spreading during application was not performed well. Further, in a recent trend, there has been an increasing desire that the cosmetics provide a natural finish. The natural finish is accomplished by forming a thin and uniform cosmetic-applied layer on the skin.

Fine particle cosmetics, which are normally formed into metal plates and the like to be used, are desired not only their characteristics as cosmetics but also for their formability. In other words, in addition to the characteristics as the makeup cosmetics accomplished by having smooth spread in only a small amount and being applied uniformly, it is desired that the cosmetics do not detach or crack when formed, and they can easily be adhered to small tools such as a sponge or a mat.

However, with conventional fine particle cosmetics, the cosmetics are easily detached or cracked, and additives must be added to achieve satisfactory formability.

Generally, the conventional fine particle cosmetics are compressed and formed to be filled into metal plates. In order to enhance the formability, methods have been applied including a method of including large amounts of additives such as oil solutions or adhesive components, a method of blending special oil components (Japanese Patent Publication Laid-open No. 2000-119134), a method of blending a specific binder resin (Japanese Patent Publication Laid-open No. 8-165221), and a method of agglutinating the fine particles with heat (Japanese Patent Publication Laid-open No. 11-228336). However, the problems of the cosmetics in which a large amount of oil solution components is blended include that they do not readily adhere to the sponge when used and that they are not smooth after use. Also, when the resin is aggregated after formation using heat, a feeling of discomfort commonly results due to the presence of the aggregated particles.

On the other hand, studies have shown that smooth spreading and an appropriate feeling of adhesion, which are desired in powder makeup cosmetics, depend upon physico-chemical properties such as the shape of materials blended into the cosmetics, a particle size distribution, surface conditions and hardness.

In recent studies, application properties and uniformity are improved through use of particles characterized by a certain primary particle size and a low span (a value found by the following equation from the particle sizes D90, D10 and D50 whose integrated values of the particle size distributions are equivalent to 90%, 10% and 50%; span=(D90−D10/D50) (Japanese Patent Publication Laid-open No. 8-277208), and with the particles whose particle size distribution (CV value) is within a certain range (Japanese Patent Publication Laid-open No. 2001-151639). Also, research has been conducted on the foundations rich in translucency enabled by keeping a prismatic reflectivity in a certain condition (Japanese Patent Publication Laid-open No. 11-209243).

Furthermore, many powder washes, especially facial washes, have recently been commercialized, and these washes are expected to have compatibility between spreadability that does not give the feeling of discomfort on the skin and appropriate massage effects. Spherical synthetic macromolecules are sometimes used as part of a feel improver or base materials in these washes.

The conventional cosmetics would include those that contain spherical polystyrene, nylon, polyacrylic, polyethylene, silicone, urethane and the like that are produced by an emulsion polymerization aggregation method, a suspension polymerization method or a precipitation polymerization method. However, because the particle size distributions of these spherical particles are wide and the surface conditions of the particles are not controlled, there has been a desire for development of cosmetics superior in spreadability when applied and superior in their formation of a uniform cosmetic layer.

Fine particle cosmetics, which have superior formability for deterring detachment or cracking of the cosmetics while restricting the use of the additives such as the oil solution components mention above to a small amount, have been especially desired.

SUMMARY OF THE INVENTION

In view of the foregoing circumstances and as a result of attentive consideration, the present inventors have found out that cosmetics, which have a specific particle size and a very narrow particle size distribution, and into which is blended a resin whose glass-transition temperature and molecular weight are lower than general-purpose resins, accomplish formability and smoothness when applied, and the forming of a uniform application layer.

Therefore, the present inventors have made it possible to solve the problems noted above by adopting the following constitution:

(1) A solid powder cosmetic, comprising 10 to 80 wt % of extender; 0.1 to 40 wt % of color pigment; and 0.5 to 80 wt % of spherical resin particles characterized by an average volume particle size of 2.0 $\mu$m to 20.0 $\mu$m, a glass-transition temperature of 10 to 100° C. and a number average molecular weight of 5000 to 20000.

(2) The solid powder cosmetic according to (1), wherein an average volume particle size distribution GSDv of the spherical resin particles is 1.3 or less, and a shape factor SF1 of the spherical resin particles is 100 to 140.

(3) The solid powder cosmetic according to (1) or (2), further including 1 to 20 wt % of an oily component.

(4) The solid powder cosmetic according to any of (1), (2) or (3), wherein a superficial index value expressed in Equation below is 2.0 or less.

[Equation]

(Superficial index value)=(Specific surface area actual measurement)/(Specific surface area calculation)

(Specific surface area calculation)/=$6\Sigma(n \times R^2)/\{\rho \times \Sigma(n \times R^3)\}$ (wherein, n=number of particles in a channel in a Coulter counter, R=channel particle size in the Coulter counter, ρ=toner density, number of channels: 16, division size: 0.1 intervals by log scale.)

(5) The solid powder cosmetic according to any of (1) to (4), wherein the spherical resin particles are an acrylic copolymer.

(6) The solid powder cosmetic according to any of (1) to (5), wherein the spherical resin particles are produced by an emulsion polymerization aggregation method.

(7) The solid powder cosmetic according to (6), wherein the spherical resin particles have micro etching surfaces.

DETAILED DESCRIPTION OF THE INVENTION

As a result of extensive research directed to cosmetics which are superior in usability and a feel after application and do not easily detach or crack during formation, the present inventors have found that superior use characteristics and formability can be accomplished when spherical resin particles are blended which have a particle size, particle size distribution and shape factor within a certain range, and which comprise a resin whose glass-transition temperature and molecular weight are lower than those of general-purpose resins.

A solid powder cosmetic in the present invention includes all cosmetics in powder form such as foundations, face powders (including a faceshadow, etc.), concealers, powders, blushes, eyeshadows, eyeliners, eyebrows, body powders, baby powders, washes, and facial washes.

The cosmetic of the present invention may have the following composition:

The solid powder cosmetic comprises 10 to 80 wt % of extender, 0.1 to 40 wt % of color pigment, and 0.5 to 60 wt % of spherical resin particles characterized by an average volume particle size of 2.0 μm to 20.0 μm, a glass-transition temperature of 10° C. to 100° C. and a number average molecular weight (Mn) of 5000 to 20000.

<Extender>

The extender is not specifically limited as long as it is one for use in the cosmetics, and examples of this could be inorganic powders such as talc, kaoline, mica, isinglass, sericite, magnesium carbonate, calcium carbonate, aluminum silicate, barium silicate, calcium silicate, magnesium silicate, magnesium, silica, zeolite, barium sulfate, and calcium phosphate, and organic powders such as silicone resin powder, cellulose powder.

When the extender is 10 wt % or less, it has a disadvantage of insufficient color tone control or of not being able to obtain sufficient brilliance. On the other hand, when the extender exceeds 80 wt %, it has a disadvantage of weakened adhesion power onto the skin or of not being able to obtain a natural color tone. It is appreciated that the extender is appropriately selected depending upon use.

<Color Pigment>

The color pigment is not specifically limited as long as it is for use in the cosmetics. As white pigments, titanium oxide and zinc oxide can be taken for example. Other color pigments can include pearl pigments such as zinc oxide, iron oxide, iron titanate, yellow iron oxide, ultramarine, Prussian blue, chromium oxide, carbon black, low titanium oxide, aluminum powder, copper powder, isinglass titanium, bismuth oxychloride and fish scale guanine, and organic pigments such as red No. 3, red No. 104, red No. 106, red No. 201, red No. 202, red No. 204, red No. 205, red No. 220, red No. 226, red No. 227, red No. 228, red No. 230, red No. 405, red No. 505, orange No. 204, orange No. 205, yellow No. 4, yellow No. 5, yellow No. 202, yellow No. 203, yellow No. 205, yellow No. 401,and blue No. 404,and chlorophyll and beta carotene. A single pigment may be used alone or two or more of these color pigments can be selected and used in used in combination, and their particle sizes and particle shapes are not limited. The powder may be blended after undergoing silicone treatment, metallic soap treatment, fatty acid treatment or interfacial active agent treatment, or treatment with acid, alkali or inorganic salts, or complex treatment of these.

When the color pigment is 0.1 wt % or less, tinting power over the skin weakens and it is not capable of functioning as a cosmetic to make the skin look beautiful. When exceeding 40 wt %, too much hiding power makes an unnatural impression, smoothness during application is lost, and stability as a cosmetic may be impaired. As the preferable blending amount of the pigment, the content of the color pigment is preferably 1 to 25 wt % for cosmetics applied to the front of a face such as a foundation or face powder, and the color pigment is preferably 10 to 40 wt % in cosmetics such as an eyeshadow for adding shadow or color to a certain area of the face.

<Spherical Resin Particles>

Particle Size:

The spherical resin particles contained in the present cosmetic have an average volume particle size of 2.0 μm to 20.0 μm, and more preferably 5.0 μm to 20.0 μm. Further, as a make-up cosmetic, 5.0 μm to 15.0 μm is preferable. If this range is exceeded, a sensation of a foreign body is caused to lead to inferior usability, or excessive stimulation is given to the skin when the spherical resin particles are applied as the cosmetic. Further, it will be difficult to control other characteristics of the present particles. If below 2.0 μm, the particles would fill facial wrinkles, thereby weakening the hiding power, while washing function tends to be decreased in the case of a washing agent.

Glass-transition temperature:

The glass-transition temperature of the spherical resin particles of the present invention is 10 to 100° C., and preferably 10 to 90° C., and more preferably 40 to 80° C. When the glass-transition temperature is below 10° C., the cosmetic is too soft. On the other hand, when the glass-transition temperature exceeds 100° C., the adhesive feeling of the cosmetic onto the skin is decreased, and a rough feeling is caused during use.

Number average molecular weight (Mn):

In the resin particles of the present invention, the number average molecular weight is 5000 to 20000,and preferably 5000 to 15000. When the resin number average molecular weight is below 5000, the cosmetic is too soft. On the other hand, when the number average molecular weight exceeds 20000, the adhesive feeling of the cosmetic onto the skin is decreased, and moreover the rough feeling is caused during use. That is, when the glass-transition temperature and the number average molecular weight exceed the ranges noted above, the resin becomes too soft or too hard, affecting usability, storability and the like.

Volume particle size distribution and shape factor SF1:

The volume particle size distribution GSDv of the spherical resin corpuscles of the present invention is 1.3 or less, and the shape factor SF1 is 100 to 140. The smoothness desired in the cosmetics or skin washes depends greatly upon the fluidity of the particles. As the shape factor SF1 approaches 100, the particle is regarded as being close to a spherical form, and the particle exceeding 140 has a big difference between a maximum length and a minimum length. If the SF1 exceeds 140, a sense of use and formability of the cosmetic become inferior. In the resin particles of the present invention, because resin corpuscles are humilis when the SF1 is in a range of 130 to 140, it is possible to feel the particles on the skin during use, which is preferable for such a cosmetic as the facial wash. On the other hand, when the SF1 is in a range of 110 to 130, the particle shape is close to a spherical form, and the fluidity on the skin surface improves, thereby enabling spreading during application in the case where the particles are blended into the make-up cosmetic, and uniform application onto the skin.

When the particle size of the spherical resin particles blended into the cosmetic is uniform as described above, and the particles close to spherical form are blended, spreading during application and the dry feeling after application can be realized. In addition, with the particle size distribution that is very sharp as described above and the particle size suitable for the cosmetics, the spherical resin particles are easy to remove from the formed cosmetics when applied while having soft physical properties, and it is possible to realize a desired smooth spread and uniformity. Further, because there is only a very small difference among particle sizes, it is possible to reduce the difference of shapes in the spherical resin particles and the difference in superficial areas, and, when a cosmetic is produced by mixing the extender, color pigment and the like, it is possible to achieve a uniform, even mix. In this way, it is possible to have equal coloring quality and functionality.

When the volume particle size distribution GSDv of the resin particles exceeds 1.3, the particle sizes are not uniform, causing the smoothness, spreadability and effects of refreshing feeling to be insufficient. As an index of the particle size distribution, it is possible to simply utilize the volume particle size distribution GSDv as indicated below, or the number particle size distribution GSDp that uses number D16 and number D84 of a volume cumulative distribution.

[Equation]

Volume particle size distribution $GSDv=(\text{Volume } D84/\text{Volume } D16)^{0.5}$ Number particle size distribution $GSDP=(\text{Number } D84/\text{Number } D16)^{0.5}$ Furthermore, the shape factor SF1 is defined as follows:

[Equation]

$SF1=(ML^2/A)\times(\pi/4)\times100$ where ML: Absolute maximum length of particle, A: Project area of particle, and these are digitalized mainly by having microscope images and scanning electronic microscope images analyzed by an image analyzing apparatus.

Superficial Index Value:

The spherical resin particles of the present invention have a superficial index value expressed in Equation below of 2.0 or less.

[Equation]

(Superficial index value)=(Specific surface area actual measurement)/(Specific surface area calculation)

(Specific surface area calculation)=$6\Sigma(n\times R^2)/\{\rho\times\Sigma(n\times R^3)\}$ (wherein, n=number of particles in a channel in a Coulter counter, R=channel particle size in the Coulter counter, ρ=toner density, number of channels: 16, division size: 0.1 intervals by log scale.)

This means that the number of divisions is determined so as to divide into 16 channels at 0.1 intervals by log scale from 1.26 μm to 50.8 μm. Concretely, division has been done with 1.26 μm or more and below 1.59 μm in channel 1, 1.59 μm or more and below 2.00 μm in channel 2, and 2.00 μm or more and below 2.52 μm in channel 3, in a way that a log value of a numerical value on a left side will be (log1.26=) 0.1, (log1.59)=0.2, 0.3 . . . 1.6.

The resin surface becomes flat and smooth as the superficial index value approaches 1.0. If the superficial index value exceeds 2.0, the surfaces of each resin become rough, which decreases the usability when contained in the cosmetics and used.

Resin:

The resin used for the resin corpuscles of the present invention is not especially limited. Specific examples of acceptable resins would include styrene such as styrene, parachlorostyrene and α-methylstyrene; acrylic monomers such as methyl acrylate, ethyl acrylate, n-propyl acrylate, lauryl acrylate and 2-ethylhexyl acrylate; methacrylic monomers such as methyl methacrylate, ethyl methacrylate, n-propyl methacrylate, lauryl methacrylate and 2-ethylhexyl methacrylate; ethylene unsaturated acid monomers such as acrylic acids, methacrylic acids and sodium sthyrenesulfonate; vinylnitriles such as acrylonitrile and methacrylonitrile; vinylethers such as vinylmethylether and vinylisobutylether; vinylketones such as vinylmethylketone, vinylethylketone and vinylisopropenylketone; homopolymers such as monomers such as olefines such as ethylene, propylene and butadiene, copolymers combining two or more of these monomers, or mixtures of these, and moreover, epoxy resin, polyester resin, polyurethane resin, polyamide resin, cellulose resin, polyether resin and the like, nonvinyl condensation resin, or mixtures of these and the vinyl resins noted above, and graft polymers obtained by polymerizing vinyl monomers under the condition in which these coexist. Among these, acrylic copolymers are preferably used as the resins blended to give a characteristic for use in skin external use compounds. Much preferably, styrene-acrylate copolymers are used.

The spherical resin particles of the present invention may have a small amount of cross-linking structure. In such a case, the content of cross-liking agent in the resin is 0.01 to 5%, more preferably 0.1 to 2%. The shape is stabilized because a small amount of cross-linking structure is applied, with the soft physical properties resulting from the glass-transition temperature and molecular weight as noted above, thereby providing more effects of preventing agglutination. If the cross-liking agent is below this range, the shape of the resin is likely to be unstable, and if this range is exceeded, the soft physical properties are likely to decrease.

As the cross-liking agent, those that are suitable in relation to the above resins may be selected. Among them, boric compounds are preferable in terms of a quick cross-linking response. For example, borax, boric acid, borate salt (e.g., orthoboric salt), $InBO_3$, $ScBO_3$, $YBO_3$, $LaBO_3$, $Mg_3(BO_3)_2$, $Co_3(BO_3)_2$, diboric acid (e.g., $Mg_2B_2O_5$, $CO_2B_2O_5$), methaboric acid (e.g., $LiBO_2$, $Ca(BO_2)_2$, $NaBO_2$, $KBO_2$), tetraboric acid (e.g., $Na_2B_4O_7 \cdot 10H_2O$), pentaboric acid (e.g., $KB_5O^3 \cdot 4H_2O$, $Ca_2B_6O_{11} \cdot 7H_2O$, $CsB_5O_5$); aldehyde compounds such as formaldehyde, glyoxal, melamine-formaldehyde (e.g., methylolmelamine, methylolmelamine alkylate) and glutaraldehyde; ketonic compounds such as diacetyl and cyclopentanedione; active halogenated compounds such as bis (2-chloroethyl urea)-2-hydroxy-4,6-dichloro-1,3,5-triazine, and 2,4-dichloro-6-S-triazine-sodium salt; active vinyl compounds such as divinylsulfonic acid, 1,3-vinylsulfonyl -2-propanol, N,N'-ethylenebis (vinylsulfonylacetamido), 1,3,5-triacryloyl-hexahydro-S-triazine; N-methylol compounds such as dimethylol urea and methyloldimethylhydantoin; resole resin; isocyanate compounds such as polyisocyanate and 1,6-hexamethylenedisocyanate; an aziridine compound disclosed in Specification U.S. Pat. No. 3,017,280 and U.S. Pat. No. 2,983,611; a carboxyimide compound disclosed in U.S. Pat. No. 3,100,704; epoxy compounds such as epoxy resin and glyceroltriglycidylether; ethyleneimino compounds such as 1,6-hexamethylene-N,N'-bisethylene urea; carboxyaldehyde halide compounds such as mucochlor acid and mocophenoxychlor acid; dioxane compounds such as 2,3-dihydroxydioxane; chrome alum, aluminum potassium alum, zirconium sulfate and chrome acid. It is appreciated that the cross-liking agent may be simply one kind or a combination of two or more kinds.

A solution of the cross-liking agent can be prepared by dissolving the cross-liking agent in water or an organic solvent. Water is generally used as the solvent that constitutes the cross-liking agent solution, and may be a water-based mixed solvent that contains the organic solvent miscible with the water. As an organic solvent, those that allow the cross-liking agent to be dissolved into may arbitrarily be used, including, for example, alcohols such as methanol, ethanol, isopropyl alcohol and glycerin; ketones such as acetone and methylethylketone, esters such as methyl acetate and ethyl acetate; aromatic solvent such as toluene; ethers such as tetrahydrofuran, and carbon halide solvent such as dichloromethane.

Preparing Method of Resin Particles:

Methods of obtaining the spherical resin particles of the present invention would include an emulsion polymerization aggregation method, a suspension polymerization method and a dispersion polymerization method. Among these, the emulsion polymerization aggregation method is preferably used. When the cross-liking agent is added, it is preferable to add it at the time of polymerizing the resin.

In the emulsion polymerization aggregation method, an ionic surfactant having a polarity reverse to that of the resin dispersion liquid based on an ionic surfactant is mixed, and heteroagglutination is caused to form the aggregated particles of the desired resin particle size, and then the agglutination is fused and coalesced by being heated to the glass-transition temperature of the resin or more before washed and dried. This preparing method makes it possible to control the particle size from an indefinite form to a spherical shape by the selection of heating temperature conditions.

Normally, the agglutinating and coalescing process in the emulsion polymerization aggregation method is performed by collectively mixing and agglutinating, so that it is possible to unite the agglutination that is in a uniform mixed state, and normally, the composition of the agglutination is uniform from the surface to the inside.

Furthermore, the spherical resin particles of the present invention are preferably applied to alkali cleaning as cleaning, after a particle forming process for fusing and coalescing the agglutination in the emulsion polymerization aggregation method noted above. By undergoing the alkali cleaning process, although a physicality index of the resin surface noted above remains the same state (i.e., the index noted above has no influence on a numerical value range), micro etching surfaces are formed which have very shallow unevenness observed by a high resolution scanning electrical microscope. As a result, a friction force against other minute cosmetic components is improved, and those other components become easy to stick to the resin surface, which inhibits the agglutination occurring after mixture, thereby making it possible to maintain dispersibility. On the other hand, adhesive power is kept low because of the very shallow unevenness, so that the cosmetic is easily separated when applied, thus not impairing the functions of the components and the spreadability imparted by the resin. The washing agent used for the alkali cleaning is not limited as long as it is, for example, a water-based solution having alkalinity. Examples could include sodium hydroxide water solution, potassium hydroxide water solution, ammonia water solution, and sodium carbonate. Especially, sodium hydroxide is preferable.

The feel of the cosmetic and characteristic deterioration are greatly concerned with the matter of coarse particle ratio. In the case of the preparation method of the present invention, the particles indicating the favorable particle size distribution GSD tend to be obtained easily, compared with normal methods, however, it is generally difficult to manage a volume particle ratio beyond 20 μm with the GSD. In the spherical resin particles of the present invention, if the ratio of the particles whose volume particle size is beyond 25 μm is 3% or more, the smooth spread would not be demonstrated on the skin, and the uniformity during application would be lost.

Other characteristics of resin particles:

The smoothness at the time of applying to the skin is obtained when the fluidity of the particles is high. As to a compression ratio, Taxation apparent gravity and solidity apparent gravity are measured by using "Powder Tester" (registered trademark) manufactured by Hosokawamicron Corporation, and the ratio between the Taxation apparent gravity and solidity apparent gravity is determined to be the compression ratio. When the compression ratio is 0.6 or less, it indicates that the particles are in the normal state and superior in the fluidity. If this range is exceeded, it will be difficult to apply the cosmetic to the skin smoothly.

Acid value has an influence on the adhesion and agglutination between the resin particles and other substances as well as on sebum resistance of the resin. When the resin that has an acid value ranging from 1.0 mg/KOH/g to 20 mg/KOH/g is blended in the cosmetic, the cosmetic can be washed out with normal soap or facial wash, which is preferable. Further, in the acid value range noted above, if other corpuscles are stuck onto the surface of the present resin particles, adhesion strength appropriate for the cosmetic or wash will be provided, and moreover the resin particles do not aggregate each other.

The resin particles used for the cosmetic of the present invention may contain other corpuscles. When other corpuscles are included, it is possible to have more of the effects of preventing re-agglutination compared with the case where the corpuscles are blended as they are, and it is possible to draw a function derived from the corpuscles while maintaining the usability based on the characteristics possessed by the resin particles in which the corpuscles are contained. The size of the corpuscles contained in the resin particles depends upon their content and the size of the resin particles containing the corpuscles, however, it is preferably 3 μm or less. If this range is exceeded, the adhesion strength onto the particle surface is weakened. The combination of containing particles and contained corpuscles especially preferable is when (diameter of containing particles)/(diameter of contained corpuscles) is 2 or more.

Methods of containing the corpuscles in the resin particles would include a method of having the corpuscles precipitated onto the resin surface, a method of having the corpuscles contained inside the resin and a method of attaching the corpuscles outside the resin.

As the method of precipitating onto the surface of the resin particles, for example, after parent aggregated particles are made in the resin particles in a first step of the agglutination process of the emulsion polymerization aggregation method, the dispersion liquid of the other corpuscles (e.g., functional corpuscles) is used in a second step of the agglutination process, thereby forming an encapsulated structure by the other corpuscles after coalescing. Metallic micro corpuscles can also be precipitated onto the resin by reducing the resin in which the other corpuscles are ion-exchanged or coordinated to a polar group of the resin in a state of ions.

Furthermore, at the time of formation of the parent aggregated particles in the first step of the emulsion polymerization aggregation method, if the other corpuscles are dispersed with the resin particles, it is possible to form the resin particles having a capsulation structure that contain the other corpuscles inside. For external attachment, it is possible to apply a method of affixing the other corpuscles onto the surface in a dry way with a mixer such as a V blender or a Henschel mixer after the resin particles are dried, and a method of, after the other corpuscles are dispersed into a liquid, having the other corpuscles added to compositions of an embrocation in a slurry state and dried and stuck onto the surface. It is also possible to dry while the slurry is spayed into dry fine particles.

The other corpuscles contained in the resin particles are not specifically limited. It means those that are generally blended into the cosmetics such as pigments, an ultraviolet masking agent, an ultraviolet absorbent, an infrared masking agent and an antibacterial agent.

Components blended into the emulsified cosmetic of the present invention other than the materials already noted are selected in accordance with intentioned use of the cosmetics, and are not limited. For example, they would include water, alcohols, a non-ionic surfactant, an anionic surfactant, a cationic surfactant, an ampholytic surfactant, an emulsifier, a binder, a dispersant, powders except for the spherical resin noted above, pigments, coloring matters, the ultraviolet masking agent, anhidrotics, the ultraviolet absorbent, an astringent agent, a coating agent, a lightweight moisturizer, cleaning components, medicinal components of various kinds, a pH adjuster, a thickener, an antioxidizing agent, a bactericide, an antibacterial agent, an antiseptic agent, beauty components and perfumes. Further, the powder may be blended after silicone treatment, metallic soap treatment, fatty acid treatment, surfactant treatment, or treatment with acid, alkali or inorganic salts, or complex treatment of these.

The method of preparation of the cosmetic is not limited. Generally, powder materials such as the extender, the color pigment and the feel improver are stirred with a ribbon blender, a powder mixer, a Henschel mixer, a ball mill, or the like. After this, oil solution components are fused and mixed, and added to a pigment mixture, and then mixed. This mixture is removed, put through a sieve to obtain particles of uniform sizes, and then filled in a container such as a metal plate. The powder material may be comminuted before stirred, and a comminuting process may be added also after the oil solution components and the powder components are mixed.

<Oily Components>

Furthermore, the oily components as the binder can be blended into the powder cosmetic of the present invention. Adding this binder makes it possible not only to improve the adhesive feeling during application but also to further strengthen the formability of the cosmetic and storability after forming. The oily components are not specifically limited as long as they are suitable for use in cosmetics, and include fats and oils, waxes, carbon hydrides, synthetic esters, fatty acids and higher alcohols. Concrete examples would be fats and oils such as camellia oil, olive oil, jojoba oil, castor oil and mink oil, waxes such as beeswax, lanoline and candelilla, carbon hydrides such as squalane, petroleum jelly, liquid paraffin and paraffin wax, fatty acids such as stearic acid and oleic acid, higher alcohols such as sethanol, stearyl alcohol and behenyl alcohol, esters such as cetylisooctanate, isopropyl myristate and glyceryl trioctanate, lanoline derivative, silicones, and fluoric oil agents. A single oil or a combination of two or more of these oils can be used. The blending amount of these binders into the cosmetic is 1 to 20 wt %. When it is below 1 wt %, the smoothness during application is damaged and the adhesive feeling on the skin after application is easy to be decreased, and when it exceeds 20 wt %, the dry feeling is decreased and the cosmetic tend to become difficult to remove from the container. A more preferable blending amount is 3 to 15 wt %.

EXAMPLES

Next, the present invention will be described in fuller detail referring to Examples and Comparative Examples. The present invention is not, however, limited to those Examples.

Resin particles were produced in the following composition.

Confection of Resin Dispersion Liquid

TABLE 1

| Composition | Resin Dispersion Liquid 1 (g) | Resin Dispersion Liquid 2 (g) |
| --- | --- | --- |
| Styrene | 540 | 400 |
| n-butylacrylate | 60 | 200 |
| Acrylic acid | 12 | 18 |
| Dodecanethiol | 12 | 24 |

With this composition, one resin made by mixing and dissolving the components of the resin dispersion liquid was dispersed and emulsified in a flask into a resin made by dissolving 13 g of the anionic surfactant "NEOGEN R" (manufactured by Dai-ichikogyo Seiyaku Co., Ltd.: sodium dodesylbenzenesulfonate) into 555 g of deionized water, and mixed slowly during ten minutes, while adding 42.8 g of deionized water in which 9 g of ammonium persulfate was dissolved, and then applied to nitrogen substitution in the flask. The flask was then heated to 70° C. in an oil bath while being stirred, and the emulsification polymerization was continued for six hours, thereby obtaining the resin corpuscle dispersion liquid.

Confection of Aggregated Particles

Using the produced resin dispersion liquid, the resin particles were produced with the following composition.

TABLE 2

| | |
| --- | --- |
| Resin corpuscle dispersion liquid: | 520 g |
| Resin corpuscle dispersion liquid (for addition): | 200 g |
| Polychlorinated aluminum 10 wt % water solution (manufactured by Asadakagaku Corporation): | 4.2 g |
| 0.02 M nitric acid: | 38 g |

Production of Manufacture Examples 1 to 6, 8:

All of the components of the resin particlesother than the resin particle dispersion liquid were placed in a round stainless steel flask to and mixed and dispersed using a homogenizer (manufactured by LKA Corporation, Ultra tarax T50). They were then heated to 60° C. while being stirred in the flask in the heating oil bath. After maintaining these conditions for the periods of time indicated in Table below at 60° C., 200 g of the resin dispersion liquid 1 was gently added, and the temperature of the heating oil bath was further raised. That temperature was maintained for fixed periods of time indicated in Table below, thereby obtaining aggregated particles.

Then, after 52 g of 1N sodium hydroxide was added to the particles as in Table below, the stainless flask was hermetically sealed and heated to 96° C. while stirring with a magnetic seal, which was maintained for seven hours, thereby fusing the aggregated particles. After these fused particles were sufficiently cleaned with deionized water of pH 6.5, they were frozen and dried to obtain the resin particles. The volume average particle size ($D_{so}$) of the fused particles was measured with a Coulter counter (manufactured by Nikkaki Corporation, TAII).

$\rho$=toner density, number of channels: 16, division size: 0.1 intervals by log scale.)

A number average molecular weight was measured with a molecular weight measuring instrument (manufactured by Tosoh Corporation, HLC-8120). The glass-transition temperature was measured with Differential Scanning Calorimeter (manufactured by Shimadzu Corporation, DSC-50), at a programming rate of 10° C. /minute.

For the compression ratio, Taxation apparent gravity X and solidity apparent gravity Y were measured with Powder Tester (manufactured by Hosokawamicron Corporation), and the calculation was performed by substituting the measured X, Y for the Equation below.

[Equation]

(Compression ratio)=(solidity apparent gravity−laxation apparent gravity X)/(solidity apparent gravity Y)

The acid value was measured in conformity with JIS K 0070.The resin powder was accurately scaled, and a specimen was put into a 300 (ml) beaker, and then 150 (ml) of a mixture liquid of toluene/ethanol (4/1) was added and dissolved. Potentiometric titration was applied to this with a 0.1 normality (N) KOH methanol solution. At the same time,

TABLE 3

|  | ME 1 | ME 2 | ME 3 | ME 4 | ME 5 | ME 6 | ME 7 | ME 8 |
|---|---|---|---|---|---|---|---|---|
| Resin dispersion liquid | 1 | 1 | 1 | 1 | 1 | 1 | — | 2 |
| Agglutinating time (minute) | 30 | 30 | 30 | 30 | 30 | 5 | — | 5 |
| Conglobation time (minute) | 9 | 7 | 4 | 9 | 2.5 | 2.5 | — | 2.5 |
| Pure cleaning | Yes | Yes | Yes | No | No | No | — | Yes |
| Average volume particle size (μm) | 6.6 | 6.7 | 6.8 | 6.5 | 6.5 | 6.5 | 8.2 | 6.7 |
| Glass-transition temperature (° C.) | 71 | 71 | 71 | 71 | 71 | 71 | 128 | 38 |
| Number average molecular weight Mn | $1.1 \times 10^4$ | $1.1 \times 10^4$ | $1.1 \times 10^4$ | $1.1 \times 10^4$ | $1.1 \times 10^4$ | $1.1 \times 10^4$ | $3.3 \times 10^3$ | $3.6 \times 10^3$ |
| Average volume perticle size distribution GSDv | 1.22 | 1.24 | 1.24 | 1.20 | 1.23 | 1.33 | 1.47 | 1.35 |
| Shape factor SF1 | 117 | 126 | 130 | 112 | 142 | 141 | 125 | 143 |
| Superficial index value | 1.37 | 1.46 | 1.39 | 2.08 | 2.11 | 2.05 | 1.23 | 2.09 |
| Compression ratio | 0.46 | 0.51 | 0.56 | 0.47 | 0.64 | 0.63 | 0.61 | 0.63 |
| Acid value (mg/KOH/g) | 5 | 5 | 5 | 5 | 5 | 5 | 1 | 9 |

ME - Manufacture Example

It should be noted that Manufacture Example 7 uses commercially available spherical polymethylmethacrylate resin. The following measurement was applied to the resin particles. The average volume particle size ($D_{so}$) and the volume particle size distribution GSDv, and the ratio of the particles whose volume particle size was 20 μm or more were measured with Laser Scattering Particle Size Distribution Analyzer (manufactured by Horiba, Ltd., LA-700), and the shape factor SF1 was measured with LUZEX image analyzer (manufactured by Nireco Corporation, LUZEXIII).

The superficial index value was calculated in accordance with the following Equations.

[Equation]

(Superficial index value)=(Specific surface area actual measurement)/(Specific surface area calculation)

(Specific surface area calculation)=$6\Sigma(n \times R^2)/\{\rho \times \Sigma(n \times R^3)\}$ (wherein, n=number of particles in a channel in the Coulter counter, R=channel particle size in the Coulter counter, measurement was applied also to blanks, and the acid value was found by the following Equation.

[Equation]

Acid value (mgKOH/g)=$((S-B) \times f \times 5.61)/W$ in Equation, W is the weight (g) of the accurately scaled resin powder, S is the used amount of KOH, B is the used amount (ml) of KOH in the measurement in the blanks, and f is a factor of OH.

Production of Solid Powder Foundation:

Using the resins of Manufacture Examples 1 to 8 produced as described, the solid powder foundations were produced in the following manner. First, the components (1) to (7) indicated in Table 4 were mixed with a Nauta mixer manufactured by Hosokawamicron Corporation, to which the mixture obtained by heating and dissolving the components (8) to (11) indicated in Table 4 was added, and were uniformly mixed. The resulting mixture was put through a sieve and then used to fill the metal plate, thereby obtaining solid powder foundations.

was put through the sieve and filled in the container, thereby obtaining solid powder eyeshadows.

TABLE 4

|  |  | Ex 1 | Ex 2 | Ex 3 | Ex 4 | Ex 5 | Ex 6 | CEx 1 | CEx 2 | CEx 3 |
|---|---|---|---|---|---|---|---|---|---|---|
| (1) | Talc | 18 | 18 | 18 | 18 | 18 | 18 | 18 | 18 | 18 |
| (2) | Mica | R | R | R | R | R | R | R | R | R |
| (3) | Titanium oxide | 10 | 10 | 10 | 10 | 10 | 10 | 10 | 10 | 10 |
| (4) | Colcothar | 0.8 | 0.8 | 0.8 | 0.8 | 0.8 | 0.8 | 0.8 | 0.8 | 0.8 |
| (5) | Yellow iron oxide | 1.8 | 1.8 | 1.8 | 1.8 | 1.8 | 1.8 | 1.8 | 1.8 | 1.8 |
| (6) | Black iron oxide | 0.4 | 0.4 | 0.4 | 0.4 | 0.4 | 0.4 | 0.4 | 0.4 | 0.4 |
| (7) | ME 1 | 22 | — | — | — | — | — | — | — | — |
| (7) | ME 2 | — | 22 | — | — | — | — | — | — | — |
| (7) | ME 3 | — | — | 22 | — | — | — | — | — | — |
| (7) | ME 4 | — | — | — | 22 | — | — | — | — | — |
| (7) | ME 5 | — | — | — | — | 22 | — | — | — | — |
| (7) | ME 6 | — | — | — | — | — | 22 | — | — | — |
| (7) | ME 7 | — | — | — | — | — | — | — | 22 | — |
| (7) | ME 8 | — | — | — | — | — | — | — | — | 22 |
| (8) | Squalane | 5 | 5 | 5 | 5 | 5 | 5 | 5 | 5 | 5 |
| (9) | Liquid paraffin | 3 | 3 | 3 | 3 | 3 | 3 | 3 | 3 | 3 |
| (10) | Vaseline | 2 | 2 | 2 | 2 | 2 | 2 | 2 | 2 | 2 |
| (11) | Antiseptic | A | A | A | A | A | A | A | A | A |
|  | Spread during application | 4.9 | 4.4 | 4.2 | 3.8 | 3.3 | 3.1 | 2.4 | 3.4 | 2.7 |
|  | Unevenness of cosmetic | 4.7 | 4.6 | 4.1 | 3.6 | 3.2 | 2.9 | 2.2 | 2.9 | 2.6 |
|  | Durability of cosmetic | 4.8 | 4.8 | 4.2 | 4.0 | 3.8 | 3.2 | 2.6 | 2.9 | 3.1 |
|  | Formability | ⊙ | ⊙ | ○ | ○ | Δ | Δ | X | X | Δ |

Ex - Example
CEx - Comparative example
ME - Manufacture example
R - Remaining amount
A - Appropriate amount It should be noted that Table 4 lists wt % values, and the "appropriate amount" refers to, for example, 0.05 wt %, and the "remaining amount" refers to a balanced amount in which addition is made to have the total amount of 100 wt %. Further, every item in the above is similar to that in Table 5 to Table 9 below.

The foundation produced in this way was applied to the skins of a panel of 20 men and women to conduct a sensory test. Evaluation standards in this test are set in the following way, and the resulting average values are shown in Table 4.
(Evaluation Standards)
(i) Spread During Application, Unevenness of Cosmetic Layer and Durability of Cosmetic
Very good . . . 5
Good . . . 4
Normal . . . 3
Bad . . . 2
Very bad . . . 1
(ii) Formability
The foundation pressed into the metal plate was dropped from a height of 50 cm and then visually evaluated.
⊙: No change
○: Cracks seen on the surface
Δ: Cracks and chips from the surface to the inside
x: Cracks and chips that make it impossible to use
Production of Solid Powder Eyeshadow:
With Manufacture Examples 1 to 5 above, the solid powder eyeshadow was manufactured. First, the compositions (1) to (5) were mixed, to which the mixture obtained by heating and dissolving the compositions (6) to (9) was added, and then comminuted and blended uniformly. This

TABLE 5

|  |  | Ex 7 | Ex 8 | Ex 9 | Ex 10 | Ex 11 | CEx 4 | CEx 5 |
|---|---|---|---|---|---|---|---|---|
| (1) | Talc | R | R | R | R | R | R | R |
| (2) | Mica | 20 | 20 | 20 | 20 | 20 | 20 | 20 |
| (3) | Titanium oxide | 10 | 10 | 10 | 10 | 10 | 10 | 10 |
| (4) | Ultramarine | 7 | 7 | 7 | 7 | 7 | 7 | 7 |
| (5) | ME 1 | 15 | — | — | — | — | — | — |
| (5) | ME 2 | — | 15 | — | — | — | — | — |
| (5) | ME 3 | — | — | 15 | — | — | — | — |
| (5) | ME 4 | — | — | — | 15 | — | — | — |
| (5) | ME 6 | — | — | — | — | 15 | — | — |
| (5) | ME 8 | — | — | — | — | — | — | 15 |
| (6) | Squalane | 5 | 5 | 5 | 5 | 5 | 5 | 5 |
| (7) | Glycerin | 3 | 3 | 3 | 3 | 3 | 3 | 3 |
| (8) | Polyoxyethylenesorbitan monooleic acid ester | 1 | 1 | 1 | 1 | 1 | 1 | 1 |
| (9) | Antiseptic | A | A | A | A | A | A | A |
|  | Spread during application | 4.5 | 4.5 | 4.3 | 4.0 | 3.1 | 2.7 | 3.0 |
|  | Unevenness of cosmetic | 4.7 | 4.5 | 4.2 | 3.7 | 3.6 | 3.0 | 3.2 |
|  | Durability of cosmetic | 4.9 | 4.8 | 4.5 | 3.9 | 3.3 | 3.2 | 3.3 |

Ex - Example
CEx - Comparative example
ME - Manufacture Example
R - Remaining amount
A - Appropriate amount The eyeshadows produced as described were applied to the skins of a panel of 20 men and women to conduct the sensory test. The evaluation standards of the test were the same as those used for evaluating the solid powder foundations, and the resulting average values are indicated in Table 5.

Production of Powder:

With the resins of Manufacture Examples 1 to 4, 6, 8 above, the powder was produced in the following manner. First, the compositions (1) to (6) were mixed, and to this was added the mixture obtained by heating and dissolving the compositions (7) to (9), and mixed uniformly. This was put through a sieve and filled in the metal plate, thereby obtaining the powder.

TABLE 6

| | | Ex 12 | Ex 13 | Ex 14 | Ex 15 | Ex 16 | CEx 6 | CEx 7 |
|---|---|---|---|---|---|---|---|---|
| (1) | Talc | 25 | 25 | 25 | 25 | 25 | 25 | 25 |
| (2) | Mica | R | R | R | R | R | R | R |
| (3) | Titanium oxide | 10 | 10 | 10 | 10 | 10 | 10 | 10 |
| (4) | Zinc oxide | 5 | 5 | 5 | 5 | 5 | 5 | 5 |
| (5) | Colcothar | 0.5 | 0.5 | 0.5 | 0.5 | 0.5 | 0.5 | 0.5 |
| (6) | ME 1 | 22 | — | — | — | — | — | — |
| (6) | ME 2 | — | 22 | — | — | — | — | — |
| (6) | ME 3 | — | — | 22 | — | — | — | — |
| (6) | ME 4 | — | — | — | 22 | — | — | — |
| (6) | ME 6 | — | — | — | — | 22 | — | — |
| (6) | ME 8 | — | — | — | — | — | — | 22 |
| (7) | Squalane | 1.5 | 1.5 | 1.5 | 1.5 | 1.5 | 1.5 | 1.5 |
| (8) | Liquid paraffin | 3 | 3 | 3 | 3 | 3 | 3 | 3 |
| (9) | Antiseptic | A | A | A | A | A | A | A |
| | Spread during application | 4.9 | 4.6 | 4.0 | 3.6 | 2.5 | 2.3 | 2.3 |
| | Unevenness of cosmetic | 4.7 | 4.6 | 4.4 | 3.9 | 2.8 | 2.6 | 2.8 |
| | Durability of cosmetic | 4.7 | 4.7 | 4.5 | 4.0 | 3.1 | 2.6 | 3.0 |

Ex - Example
CEx - Comparative example
ME - Manufacture Example
R - Remaining amount
A - Appropriate amount The powder produced in this way was applied to the skins of a panel of 20 men and women to conduct the sensory test. The evaluation standards of the test were the same as those used for the solid powder foundation, and the resulting average values are indicated in Table 6.

Production of Blush:

With the resins of Manufacture Examples 1 to 4, 6, 8 above, blushes were produced in the following manner. First, the compositions (1) to (6) were mixed, and to this mixture was added the mixture obtained by heating and dissolving the compositions (7) to (9), and then mixed uniformly. This mixture was put through a sieve and filled in the metal plate, thereby obtaining the blushes.

TABLE 7

| | | Ex 17 | Ex 18 | Ex 19 | Ex 20 | Ex 21 | CEx 8 | CEx 9 |
|---|---|---|---|---|---|---|---|---|
| (1) | Talc | 25 | 25 | 25 | 25 | 25 | 25 | 25 |
| (2) | Mica | R | R | R | R | R | R | R |
| (3) | Titanium oxide | 3 | 3 | 3 | 3 | 3 | 3 | 3 |
| (4) | Mica covered titanium oxide | 3 | 3 | 3 | 3 | 3 | 3 | 3 |
| (4) | Colcothar | 1 | 1 | 1 | 1 | 1 | 1 | 1 |
| (5) | Red pigment | 1.5 | 1.5 | 1.5 | 1.5 | 1.5 | 1.5 | 1.5 |
| (6) | ME 1 | 22 | — | — | — | — | — | — |
| (6) | ME 2 | — | 22 | — | — | — | — | — |
| (6) | ME 3 | — | — | 22 | — | — | — | — |
| (6) | ME 4 | — | — | — | 22 | — | — | — |
| (6) | ME 6 | — | — | — | — | 22 | — | — |
| (6) | ME 8 | — | — | — | — | — | — | 22 |
| (7) | Squalane | 1.5 | 1.5 | 1.5 | 1.5 | 1.5 | 1.5 | 1.5 |
| (8) | Liquid paraffin | 3 | 3 | 3 | 3 | 3 | 3 | 3 |
| (9) | Antiseptic | A | A | A | A | A | A | A |
| | Spread during application | 4.7 | 4.3 | 4.2 | 3.7 | 3.0 | 2.2 | 2.8 |
| | Unevenness of cosmetic | 4.7 | 4.4 | 4.1 | 3.5 | 2.6 | 2.1 | 2.3 |
| | Durability of cosmetic | 4.7 | 4.5 | 4.5 | 3.7 | 2.6 | 2.2 | 2.5 |

Ex - Example
CEx - Comparative example
ME - Manufacture Example
R - Remaining amount
A - Appropriate amount The blushes produced in this way were applied to the skins of a panel of 20 men and women to conduct the sensory test. The evaluation standards of the test were the same as those used for the solid powder foundations, and the resulting average values are indicated in Table 7.

Production of Solid Powder Eyeliner:

With styrene-butylacrylate resins of Manufacture Examples 1 to 4, 6 and 8 manufactured as above, the eyeliners were produced in the following manner. First, the compositions (1) to (5) were mixed, to which the mixture obtained by heating and dissolving the compositions (6) to (9) was added, and then mixed uniformly. This mixture was put through a sieve and filled in the metal plate, thereby obtaining the eyeliners.

TABLE 8

| | | Ex 22 | Ex 23 | Ex 24 | Ex 25 | Ex 26 | CEx 10 | CEx 11 |
|---|---|---|---|---|---|---|---|---|
| (1) | Talc | 20 | 20 | 20 | 20 | 20 | 20 | 20 |
| (2) | Mica | R | R | R | R | R | R | R |
| (3) | Titanium oxide | 3 | 3 | 3 | 3 | 3 | 3 | 3 |
| (4) | Ultramarine | 5 | 5 | 5 | 5 | 5 | 5 | 5 |
| (5) | ME 1 | 22 | — | — | — | — | — | — |
| (5) | ME 2 | — | 22 | — | — | — | — | — |
| (5) | ME 3 | — | — | 22 | — | — | — | — |
| (5) | ME 4 | — | — | — | 22 | — | — | — |
| (5) | ME 6 | — | — | — | — | 22 | — | — |
| (5) | ME 8 | — | — | — | — | — | — | 22 |
| (6) | Squalane | 10 | 10 | 10 | 10 | 10 | 10 | 10 |
| (7) | Liquid paraffin | 7 | 7 | 7 | 7 | 7 | 7 | 7 |
| (8) | Polyoxy-ethylene-sorbitan monooleic acid ester | 5 | 5 | 5 | 5 | 5 | 5 | 5 |
| (9) | Antiseptic | A | A | A | A | A | A | A |
| | Spread during application | 4.7 | 4.2 | 4.0 | 3.2 | 2.2 | 2.0 | 2.2 |
| | Unevenness of cosmetic | 4.8 | 4.6 | 4.4 | 3.8 | 3.3 | 2.9 | 2.9 |
| | Durability of cosmetic | 4.9 | 4.7 | 4.7 | 3.6 | 3.5 | 3.0 | 3.4 |

Ex - Example
CEx - Comparative example
ME - Manufacture example
R - Remaining amount
A - Appropriate amount The eyeliners produced in this way were applied to the skins of a panel of 20 men and women to conduct the sensory test. The evaluation standards of the test were the same as those used for the solid powder foundations, and the resulting average values are indicated in Table 8.

Production of Solid Powder Facial Wash:

With the styrene-butylacrylate resins of Manufacture Examples 1 to 4, 6, 8 manufactured as above, the powder facial wash was uniformly stirred and mixed with the materials of the following manner and put through a sieve and then filled in the container, thereby obtaining the facial washes.

TABLE 9

| | | Ex 27 | Ex 28 | Ex 29 | Ex 30 | Ex 31 | CEx 12 | CEx 13 |
|---|---|---|---|---|---|---|---|---|
| (1) | Titanium oxide | 1 | 1 | 1 | 1 | 1 | 1 | 1 |
| (2) | ME 1 | 15 | — | — | — | — | — | — |
| (2) | ME 2 | — | 15 | — | — | — | — | — |
| (2) | ME 3 | — | — | 15 | — | — | — | — |
| (2) | ME 4 | — | — | — | 15 | — | — | — |
| (2) | ME 6 | — | — | — | — | 15 | — | — |
| (2) | ME 8 | — | — | — | — | — | — | 15 |
| (3) | Sodium lauroyl glutamate | 7 | 7 | 7 | 7 | 7 | 7 | 7 |
| (4) | Sodiums myristoyl glutamate | 7 | 7 | 7 | 7 | 7 | 7 | 7 |
| (5) | Potassium myristate | 5 | 5 | 5 | 5 | 5 | 5 | 5 |
| (6) | Glucose | 0.3 | 0.3 | 0.3 | 0.3 | 0.3 | 0.3 | 0.3 |
| (7) | Water-soluble collagen | 0.1 | 0.1 | 0.1 | 0.1 | 0.1 | 0.1 | 0.1 |
| (8) | Disodium ascorbate nitrate | 0.1 | 0.1 | 0.1 | 0.1 | 0.1 | 0.1 | 0.1 |
| (9) | Antiseptic | A | A | A | A | A | A | A |
| (10) | Talc | R | R | R | R | R | R | R |
| | Spread during application | 4.6 | 4.1 | 4.0 | 3.6 | 2.8 | 3.7 | 2.6 |
| | Cleaning effects | 4.2 | 4.5 | 4.7 | 3.8 | 3.8 | 2.6 | 3.2 |

Ex - Example
CEx - Comparative example
ME - Manufacture example
R - Remaining amount
A - Appropriate amount The solid powder facial washes produced as described were spread with tepid water, and applied to the skins of a panel of 20 men and women to conduct the sensory test. For spreading, the evaluation standards of the test were the same as those of the solid powder foundations. As to washing effects, the following standards were used, and the resulting average values are indicated in Table 9.

(Evaluation Standards on Washing Effects)
Sufficient washing effects can be obtained . . . 5
Washing effects can be obtained . . . 4
Normal . . . 3
Washing effects felt very much . . . 2
Washing effects not felt . . . 1

Test Results:

According to the results of the sensory tests, it is apparent that the powder cosmetics in which the resin particles of the present invention are blended are superior in smoothness, perceived feel during application including spreadability, and in uniformity of the cosmetic layer formed by being applied on the surface of the skin, and further superior in formability to the comparative articles. Furthermore, in the washes, in addition to the fact that spreading quality superior to that of the comparative articles, it is evident that using the spherical resin particles that have unevenness of a certain degree can produce massage effects and enhance washing effects.

The solid powder cosmetic of the present invention comprises resin particles characterized by specific particle size and narrow particle size distribution, and in that it is made from resins whose molecular weight is smaller than that of general-purpose resins and produced by blending the extender and color pigment. Further, the spherical resin particles in the present invention include a spherical form to the shapes having minute unevenness, and the surfaces of the resin particles are very flat and smooth. Therefore, for example, the cosmetics in which the spherical resin particles are blended demonstrate smooth spread when applied, and have a dry feel, and moreover enable uniform application. In addition, cosmetics that use the spherical resin particles having minute unevenness can provide an appropriate feeling of particles while maintaining characteristics of spreadability and feel because of the physical properties described above, thereby imparting a massage effect.

What is claimed is:

1. A solid powder cosmetic, comprising:
   10 to 80 wt % of extender;
   0.1 to 40 wt % of color pigment; and
   0.5 to 80 wt % of spherical resin particles whose average volume particle size is 2.0 to 20.0 $\mu$m, glass-transition temperature is 10 to 100° C. and number average molecular weight is 5000 to 20000, wherein a volume particle size distribution GSDv of the spherical resin particles is 1.3 or less, and a share factor SF1 is 110 to 140.

2. The solid powder cosmetic according to claim 1, further including 1 to 20 wt % of an oily component.

3. The solid powder cosmetic according to claim 1, wherein a superficial index value of the spherical resin particles expressed in an equation below is 2.0 or less.

(Superficial index value)=(Specific surface area actual measurement)/(Specific surface area calculation)

(Specific surface area calculation)=$6\Sigma(n \times R^2)/\{\rho \times \Sigma(n \times R^3)\}$, wherein n=number of particles in a channel in a Coulter counter, R=channel particle size in the Coulter counter, $\rho$=toner density, number of channels: 16, division size: 0.1 intervals by log scale.

4. The solid powder cosmetic according to claim 1, wherein the spherical resin particles are formed from an acrylic copolymer.

5. The solid powder cosmetic according to claim 1, wherein the spherical resin particles are produced by an emulsion polymerization aggregation method.

6. The solid powder cosmetic according to claim 4, wherein the spherical resin particles have micro etching surfaces.

7. The solid powder cosmetic according to claim 1, wherein the average volume particle size of the spherical resin particles is 5.0 $\mu$m to 15.0 $\mu$m.

8. The solid powder cosmetic according to claim 1, wherein the glass-transition temperature of the spherical resin particles is in a range of 40 to 80° C.

9. The solid powder cosmetic according to claim 1, wherein the number average molecular weight of the spherical resin particles is in a range of 5000 to 15000.

10. The solid powder cosmetic according to claim 1, wherein a compression ratio of the spherical resin particles is 0.6 or less.

11. The solid powder cosmetic according to claim 2, including 3 to 15 wt % of the oily component.

12. The solid powder cosmetic according to claim 1, wherein the extender is selected from talc, kaoline, mica, isinglass, sericite, magnesium carbonate, calcium carbonate, aluminum silicate, barium silicate, calcium silicate, magnesium silicate, magnesium, silica, zeolite, barium sulfate, calcium phosphate, silicone resin powder and cellulose powder.

13. The solid powder cosmetic according to claim 1, for use in cosmetics applied to the front of a face in which the content of the color pigment is 1 to 25 wt %.

14. The solid powder cosmetic according to claim 1, for use in cosmetics for adding a shadow or a color in which the content of the color pigment is 10 to 40 wt %.

15. The solid powder cosmetic according to claim 1 for washing, wherein the SF1 of the spherical resin particles is in a range of 130 to 140.

16. The solid powder cosmetic according to claim 1 for make-up, wherein the SF1 of the spherical resin particles is in a range of 110 to 130.

* * * * *